US011185685B2

(12) United States Patent
Henle et al.

(10) Patent No.: US 11,185,685 B2
(45) Date of Patent: Nov. 30, 2021

(54) ELASTIC NEURAL ELECTRODE AND METHOD FOR FABRICATING THE SAME

(71) Applicant: CorTec GmbH, Freiburg (DE)

(72) Inventors: Christian Henle, Freiburg (DE); Martin Schuettler, Emmendingen (DE); Fabian Kohler, Freiburg (DE); Miguel Ulloa, Freiburg (DE); Juan Sebastian Ordonez, Freiburg (DE); Matthias Mueller, Freiburg (DE)

(73) Assignee: CorTecGmbH, Freiburg (DE)

( * ) Notice: Subject to any disclaimer, the term of this patent is extended or adjusted under 35 U.S.C. 154(b) by 351 days.

(21) Appl. No.: 16/250,474

(22) Filed: Jan. 17, 2019

(65) Prior Publication Data
US 2019/0143101 A1 May 16, 2019

Related U.S. Application Data

(63) Continuation of application No. PCT/EP2017/068125, filed on Jul. 18, 2017.

(30) Foreign Application Priority Data

Jul. 18, 2016 (DE) ..................... 10 2016 113 215.2

(51) Int. Cl.
A61N 1/05 (2006.01)
A61N 1/375 (2006.01)

(52) U.S. Cl.
CPC ........... A61N 1/0551 (2013.01); A61N 1/375 (2013.01)

(58) Field of Classification Search
CPC .............................. A61N 1/0551; A61N 1/375
See application file for complete search history.

(56) References Cited

U.S. PATENT DOCUMENTS

| 2006/0225274 | A1 | 10/2006 | Greenberg et al. |
| 2009/0124965 | A1 | 5/2009 | Greenberg et al. |
| 2014/0039589 | A1 | 2/2014 | Seymour et al. |
| 2014/0046417 | A1 | 2/2014 | Schüttler et al. |
| 2014/0128954 | A1 | 5/2014 | Schüttler et al. |

FOREIGN PATENT DOCUMENTS

| DE | 102012010825 B3 | 3/2013 |
| EP | 2696934 A1 | 2/2014 |
| JP | 2007-167636 A | 7/2007 |
| WO | 97/28668 A1 | 8/1997 |

(Continued)

OTHER PUBLICATIONS

Notice of Reasons for Rejection issued for corresponding Japanese Patent Application No. 2019-502198, dated Sep. 23, 2020, with English translation attached.

(Continued)

Primary Examiner — Mark W. Bockelman
(74) Attorney, Agent, or Firm — Myers Wolin, LLC

(57) ABSTRACT

An elastic neural electrode is provided, having at least one planar metal layer which comprises conductive material and which is placed on an elastomer layer (PDMS), wherein, for reinforcement of the electrode, a high-tensile-strength polymer layer, in particular parylene layer is applied directly onto the at least one metal layer, the high-tensile-strength polymer layer, in particular parylene layer being the outermost layer of the electrode.

16 Claims, 3 Drawing Sheets

(56) References Cited

FOREIGN PATENT DOCUMENTS

WO    2012140262 A1    10/2012

OTHER PUBLICATIONS

International Search Report issued by the International Search Authority for corresponding International Application No. PCT/EP2017/068125, dated Oct. 5, 2017.

Suaning et al., "Fabrication of multi-layer, high-density micro-electrode arrays for neural stimulation and bio-signal recording," Proceedings of the 3rd International IEEE EMBS Conference on Neural Engineering, May 2-5, 2007, pp. 5-8, ThA1.2, Kohala Coast, Hawaii, USA.

Schuettler et al., "Stretchable Tracks for Laser-Machined Neural Electrode Arrays," 31st Annual International Conference of the IEEE EMBS, Sep. 2-6, 2009, pp. 1612-1615, Minneapolis, Minnesota, USA.

Henle et al. "Mechanical Characterization of Neural Electrodes based on PDMS-Parylene C-PDMS Sandwiched System," 33rd Annual International Conference of the IEEE EMBS, Aug. 30-Sep. 3, 2011, pp. 640-643, Boston, Massachusetts, USA.

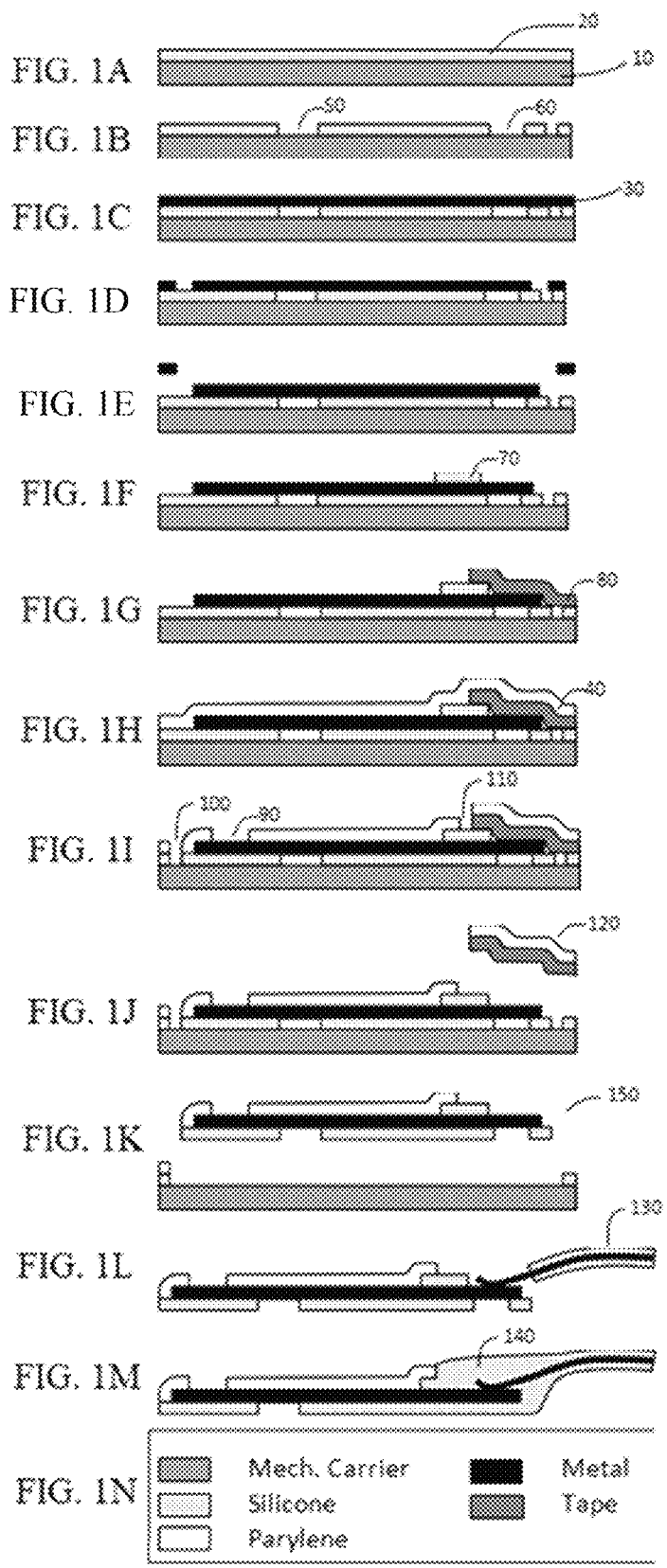

ELASTIC NEURAL ELECTRODE AND METHOD FOR FABRICATING THE SAME

CROSS REFERENCE TO RELATED APPLICATIONS

This application is a continuation of International Application No. PCT/EP2017/068125, filed on Jul. 18, 2017, which takes priority from German Application No. 10 2016 113 215.2, filed on Jul. 18, 2016, the contents of each of which are incorporated by reference herein.

TECHNICAL FIELD

The invention relates to an elastic neural electrode, and to a method of fabrication of the same. It relates in particular to such an electrode which is able to withstand high mechanical forces

BACKGROUND

Known elastic neural electrodes comprise the layering sequence elastomer-metal-elastomer with silicone rubber being the top elastomer layer. Electrically conducting tracks and contact pads are generated by cutting them out of a metal foil. These tracks and pads are embedded in a silicone elastomer. Since the silicone is very elastic, it cannot protect the delicate metal tracks against strain and other mechanical load as applied, e.g. during implantation surgery. Therefore, in the art, an additional layer is provided whose function is to set the mechanical properties of the neural electrode and to protect the metal structures. This additional layer is a high tensile strength polymer foil, e.g., parylene-C, or a mesh made from polymeric fibers. This layer acts as mechanical reinforcement, e.g. strain relieve in order to minimize the force reaching the delicate metal tracks. This layer is embedded into a elastomer layer, located i.e. between the metal layer and the bottom elastomer layer.

This renders the fabrication process complicated, and the additional reinforcement layer makes the neural electrode thicker than without such reinforcement layer. Another disadvantage is that the tough reinforcement layer, which defines the mechanical neutral axis of the electrode array, is located in a different layer than the metal. Bending of the electrode array will still lead to tensile and/or compressive forces in the metal layer, risking the integrity of the metal structures.

SUMMARY

It is an object to provide a neural electrode which is, on the one hand, flexible but thin and robust enough, and, on the other hand, less expensive to fabricate.

This object is solved by the elastic neural electrode, and the method of fabricating an elastic neural electrode with the features of the respective independent claim. Advantageous embodiments are defined in the respective dependent claims.

Accordingly, provided is an elastic neural electrode, having at least one planar metal layer which comprises conductive material and which is placed on an elastomer layer (PDMS), wherein, for reinforcement of the electrode, a high-tensile-strength polymer layer, in particular parylene layer is applied directly onto the at least one metal layer, the high-tensile-strength polymer layer, in particular parylene layer being the outermost layer of the electrode.

Thus, the known process of fabricating neural electrodes based on metalized elastomer is simplified since the layer which is placed on the metal layer is a multi-functional layer, serving for both protection (electrical isolation) and mechanical reinforcement, or only for mechanical reinforcement. Furthermore, since a great part of the reinforcement layer is located between the metal structures and with this, the neutral axis is in the layer of the metal, meander-like metal tracks are not necessary anymore, so that it is possible to fabricate neural electrodes with a higher integration level, increasing the amount of tracks and/or electrode contacts per area.

Once produced, an electrode array is usually connected to wires or electronics by welding, soldering or wire bonding at a dedicated interconnection location (welding area). Once the array is connected, the electrical contacts of the welding area have to be electrically sealed against each other and against the environment by a polymeric seal. This seal is established using a silicone rubber adhesive, which permanently adheres to silicone rubber itself, however a permanent bond to the high-tensile-strength polymer layer, in particular parylene cannot be warranted. In order to avoid a material transition, where silicone is applied on top of high-tensile-strength polymer, in particular parylene, process steps f-j in FIGS. 1F-1J are introduced which ensure that the function of the electrode array never relies on the adhesion of silicone to parylene but only on the adhesion of parylene to silicone and silicone to silicone.

The method for fabrication of an elastic neural electrode, in particular as defined above, comprises the following steps:
- applying an elastomer layer onto the release carrier
- structuring the elastomer layer using a laser beam
- laminating a metal layer onto the elastomer layer
- structuring the metal layer using a laser beam
- removing excess metal
- applying an elastomer layer onto the metal layer, thus defining an edge of a welding site
- applying a masking tape at the welding site
- deposing a parylene layer directly onto the metal layer, elastomer layer and masking tape
- structuring openings, cutting-free the masking tape outer contour of the planar electrode using a laser beam
- removing the masking tape, exposing the welding area
- removing the electrode from the mechanical carrier
- welding the wires to the electrode
- sealing the welding area with an elastomer Additional metal layers may be provided in the neural electrode. However, as the outermost (top) layer, always the high-tensile-strength polymer, in particular parylene, is applied.

BRIEF DESCRIPTION OF THE DRAWINGS

The invention and embodiments thereof will be described in more detail with reference to the drawings, wherein FIGS. 1A-M illustrate the processing steps, layer view;

FIG. 1N provides a key for the shading used in FIGS. 1A-M.

DETAILED DESCRIPTION

Figure 2A:
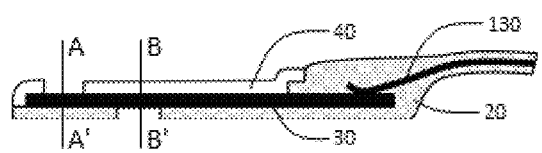
FIG. 2A illustrates a neural electrode.

Referring to FIGS. 1A-M, the sequence of process steps which can be applied for fabricating the neural electrodes as described.

First, a mechanical carrier 10 is coated with a layer 20 of silicone rubber (elastomer layer) step a).

The silicone 20 is removed with a laser at locations where electrode sites are going to be and at area of welding wires to the metal (step b).

A metal foil 30 is laminated to the silicone layer 20 (step c), and the perimeter of electrode track, weld pads and electrode sites are cut with a laser (step d).

Excess metal foil is removed (step e), and at the location of transition (i.e., an edge) from electrode site area to a welding area, a layer 70 of liquid silicone rubber is deposited and cured (step f).

The entire weld area as well as a part of the silicone 70 that has been deposited in the previous process step is covered by masking tape 80 (step g).

The entire structure is coated with parylene 40 (polymer layer) (step h).

Using a laser, the perimeter of the electrode array is cut, electrode sites 110 are opened and the masking tape is cut free (step i).

The masking tape along with parylene coated thereon 120 is removed, exposing the welding area (step j).

The electrode array 150 is lifted off from the mechanical carrier 10 (step k), which is discarded. Wires 130 are welded to the individual tracks at the welding area (step l,) and all exposed metal in the welding area is sealed with liquid silicone (step m) which is allowed to cure.

Usually, medical grade silicone rubber is used as elastomer. The metal foil can be made from stainless steel, platinum, platinum-iridium, or any material suitable for neural electrode fabrication.

The coating method is a chemical vapor deposition of parylene (standard operation procedure for deposition of parylene).

Figure 2B:
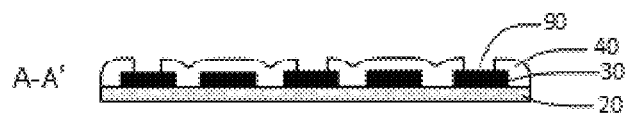
FIGS. 2B and 2C illustrate cross sectional views of FIG. 2A.
Figure 2C:
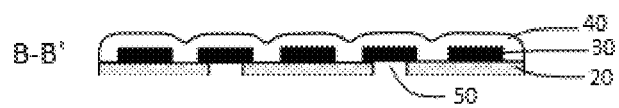
Figure 2D:
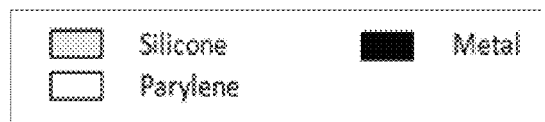
FIG. 2D provides a key for the shading used in FIGS. 2A-C.

FIGS. 2A-C show cross sections through an electrode array, illustrating that the electrode array may consist of multiple tracks which can be exposed to the top, refer to opening 90 (by removing the parylene), to the bottom, refer to opening 50 (by removing the silicone), or to both sides, as it is illustrated in FIG. 2A.

Figure 3A:
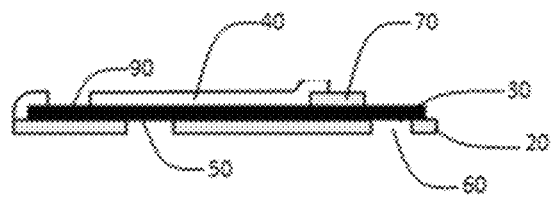
FIGS. 3A and 3B illustrate a side view and a top view respectively of an electrode array before wire assembly and sealing.
Figure 3B:
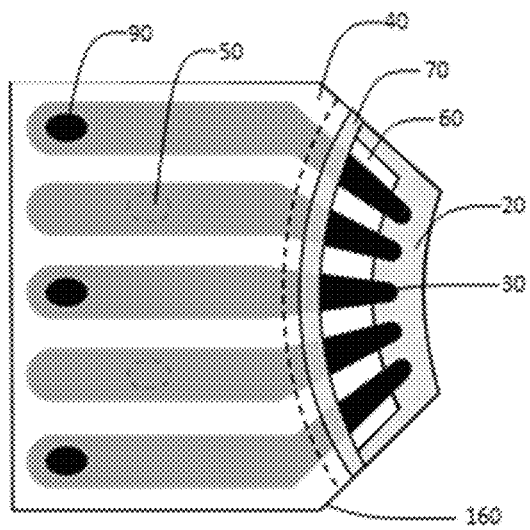
Figure 3C:
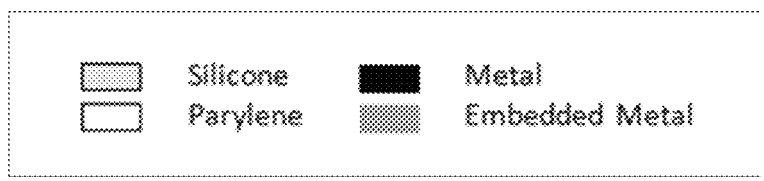
FIG. 3C illustrates a key for the shading used in FIGS. 3A-B.

FIGS. 3A-B illustrate the electrode array before wire assembly and sealing. FIG. 3A is a side view, and FIG. 3B is a top view onto the electrode array.

LIST OF REFERENCE NUMERALS

10 Mechanical Carrier
20 Silicone
30 Metal Foil
40 high-tensile-strength polymer, in particular Parylene
50 Electrode Site Facing Down (Window in Silicone)
60 Welding Area
70 Silicone Island
80 Masking Tape
90 Electrode Site Facing Up (Window in Parylene)
100 Trench Defining the Perimeter of Electrode Array
110 Trench, separating Tape from Rest of Parylene
120 Masking Tape with Parylene
130 Wire with insulation
140 Silicone Seal
150 Electrode Array before Wire Assembly and Sealing
160 Perimeter of Electrode Array

What is claimed is:

1. An elastic neural electrode, comprising:
   at least one planar metal layer arranged on an elastomer layer,
   wherein an edge of a welding area of the planar metal layer is defined by an elastomer layer applied on the welding area,
   wherein a high-tensile-strength polymer layer is arranged directly on the at least one metal layer and the elastomer layer applied on the edge of the welding area,
   the high-tensile-strength polymer layer being an outermost layer of the electrode, and wherein all exposed metal of the welding area is sealed with an elastomer adhesive.

2. The electrode of claim 1, wherein the elastomer layer, the at least one planar metal layer, and the high-tensile-strength polymer layer are arranged as a stack.

3. The electrode of claim 1, wherein the high-tensile-strength polymer layer has at least one window to the at least one metal layer.

4. The electrode of claim 1, wherein the elastomer layer has at least one window to the at least one metal layer.

5. The electrode of claim 1, wherein the at least one metal layer is embedded in the elastomer layer.

6. The electrode of claim 1, wherein the at least one metal layer comprises meander-like conductive paths.

7. The electrode of claim 1, wherein the high-tensile-strength polymer layer is structured using a laser beam.

8. The electrode of claim 1, wherein the elastomer layer comprises a medical grade silicone rubber, and wherein the metal layer comprises one of stainless steel, platinum, platinum-iridium or gold, and wherein the high-tensile-strength polymer layer comprises Parylene.

9. A neural electrode array comprising:
   a number of electrodes for electrical interfacing with biological tissue as defined in claim 1, wherein the electrodes have at least one layer in common.

10. The electrode of claim 1, wherein the high-tensile-strength polymer layer is a parylene layer.

11. A method for fabrication of an elastic neural electrode of claim 1 comprising the following steps:
    applying an elastomer layer onto a release carrier;
    structuring the elastomer layer using a laser beam;
    laminating at least one metal layer onto the elastomer layer;
    structuring the at least one metal layer using a laser beam;
    removing excess metal;
    applying an elastomer layer onto the at least one metal layer, thus defining an edge to a welding area;
    applying a masking tape at the welding area;
    deposing a high-tensile-strength polymer layer directly onto the at least one metal layer, and onto the elastomer layer, and onto the masking tape;
    structuring openings and cutting-free the masking tape using a laser beam;
    removing the masking tape, exposing the welding area;
    removing the electrode from the mechanical carrier;
    welding the wires to the electrode;
    sealing the welding area with an elastomer.

12. The method of claim 11, wherein the shaping of the at least one metal layer, removing of the excess metal, the partial removing of the third elastomer, or the cutting out of the outer contour is achieved by means of laser processing.

13. The method of claim 11, wherein an additional step of printing information onto the high-tensile-strength polymer layer is carried out.

14. The method of claim 11, wherein an additional step of perforating the high-tensile-strength polymer layer is carried out.

15. The method of claim 11, wherein the polymer layer is a parylene layer.

16. The electrode of claim 15, wherein the parylene layer is vapour-deposited onto the at least one metal layer.

* * * * *